United States Patent [19]

Achey et al.

[11] Patent Number: 5,616,825
[45] Date of Patent: Apr. 1, 1997

[54] EXHAUST SENSOR INCLUDING A CERAMIC TUBE IN METAL TUBE PACKAGE

[75] Inventors: David E. Achey, Grand Blanc; Gary E. Thoman, Fenton, both of Mich.

[73] Assignee: General Motors Corporation, Detroit, Mich.

[21] Appl. No.: 583,199

[22] Filed: Jan. 4, 1996

Related U.S. Application Data

[63] Continuation of Ser. No. 313,687, Sep. 27, 1994, abandoned.

[51] Int. Cl.$^6$ ................................................ G01N 27/04
[52] U.S. Cl. ..................... 73/23.31; 73/31.05; 204/426; 204/424; 338/34
[58] Field of Search .............................. 73/23.31, 23.32, 73/31.05, 31.06; 204/424, 426; 338/34, 221, 229, 230

[56] References Cited

U.S. PATENT DOCUMENTS

| | | | |
|---|---|---|---|
| 4,040,930 | 8/1977 | Dillon | 204/426 |
| 4,206,173 | 6/1980 | Yamaguchi et al. | 338/34 |
| 4,225,842 | 9/1980 | Schlesselman et al. | 338/34 |
| 4,294,801 | 10/1981 | Segawa et al. | 338/34 |
| 4,403,207 | 9/1983 | Murphy et al. | 338/34 |
| 4,535,316 | 8/1985 | Wertheimer et al. | 73/23.32 |
| 4,620,437 | 11/1986 | Takami et al. | 73/31.05 |
| 4,656,863 | 4/1987 | Takami et al. | 73/31.05 |
| 4,802,369 | 2/1989 | Morii | 204/424 |
| 4,958,514 | 9/1990 | Takami | 338/34 |
| 5,031,445 | 7/1991 | Kato et al. | 204/424 |
| 5,039,972 | 8/1991 | Kato et al. | 338/34 |
| 5,089,133 | 2/1992 | Kato et al. | 204/424 |
| 5,139,639 | 8/1992 | Holleboom | 204/424 |
| 5,228,975 | 7/1993 | Yamada et al. | 204/424 |
| 5,246,562 | 9/1993 | Weyl et al. | 204/424 |
| 5,329,806 | 7/1994 | McClanahan et al. | 73/31.05 |

FOREIGN PATENT DOCUMENTS

| | | |
|---|---|---|
| 398579 | 11/1990 | European Pat. Off. . |
| 3922331 | 1/1991 | Germany . |
| WO-A-9208127 | 5/1992 | WIPO . |

OTHER PUBLICATIONS

Webster's II New Riverside University Dictionary, 1988, p. 1135.

*Primary Examiner*—Hezron E. Williams
*Assistant Examiner*—Daniel S. Larkin
*Attorney, Agent, or Firm*—Cary W. Brooks

[57] ABSTRACT

The invention includes a sealing system for a heated flat plate exhaust gas sensor having a plurality of alternating layers of glass and steatite surrounding a flat plate sensing element. A ceramic tube surround the plurality of layers. The ceramic tube is carried in a tubular-shaped metal housing.

7 Claims, 3 Drawing Sheets

EXHAUST SENSOR INCLUDING A CERAMIC TUBE IN METAL TUBE PACKAGE

This is a continuation of application Ser. No. 08/313687 filed on Sep. 27, 1994, now abandoned.

FIELD OF THE INVENTION

This invention relates to exhaust sensors, and more particularly to a flat plate exhaust sensor having a ceramic tube in a metal tube package.

BACKGROUND OF THE INVENTION

FIG. 1 illustrates a flat plate automotive exhaust sensor of the prior art. The exhaust sensor includes a heated flat plate sensing element 138 which is carried in a tubular housing 116 and held in position by a first cement composition 140, glass seal 142 and a second cement composition 144, each of which extends from the flat plate heating element to the tubular wall 116 of the sensor. The heated flat plate sensing element includes an air reference channel formed therein and is positioned within the sensor to provide communication with an air source in the upper portion of the sensor. A glass seal prevents exhaust gas from travelling from the lower end of the sensor through the tubular housing and into the upper portion portion of the sensor. A glass seal prevents exhaust gas from travelling from the lower end of the sensor through the tubular housing and into the upper portion of the sensor to communicate with the air in the air reference channel of the electrolyte body. Glass seals are desirable because they are easily formed by firing glass frit in a furnace. Such sensors are used to monitor constituents in an automotive combustion engine exhaust gas stream such as oxygen, and to adjust the operation of the engine including the air fuel ratio.

However, the glass seal, heated flat plate sensing element and the tubular shell have different thermal coefficients of expansion. When the sensor is exposed to high temperatures associated with combustion engine exhaust, the glass seal, heated flat plate sensing element and tubular shell expand and contract at different rates. This often results in leakage paths between the glass seal and the tubular shell, the flat plate sensor element being damaged by expansion of the glass seal, or the flat plate exhaust sensor coming loose within the housing.

The present invention overcomes many of the deficiencies of the prior art sensors.

SUMMARY OF THE INVENTION

The invention includes a sealing system for a heated flat plate exhaust gas sensor having a plurality of alternating layers of glass and steatite surrounding a flat plate sensing element. A ceramic tube surround the plurality of layers. The ceramic tube is carried in a tubular-shaped metal housing.

These and other objections, features and advantages of the present invention will be apparent from the following brief description of the drawings, detailed description and appended claims and drawings.

DETAILED DESCRIPTION

Figure 1:
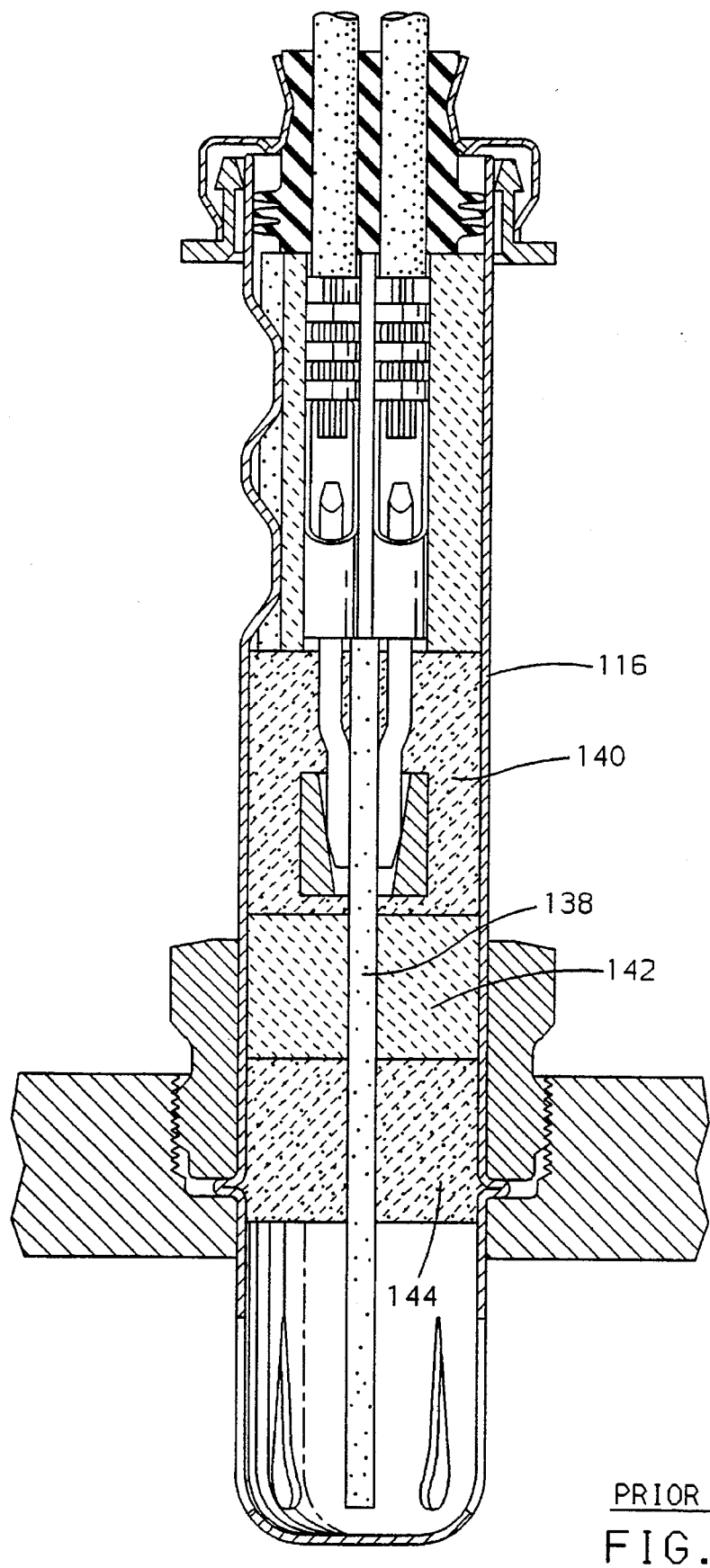
FIG. 1 illustrates a prior art exhaust sensor.
Figure 2:
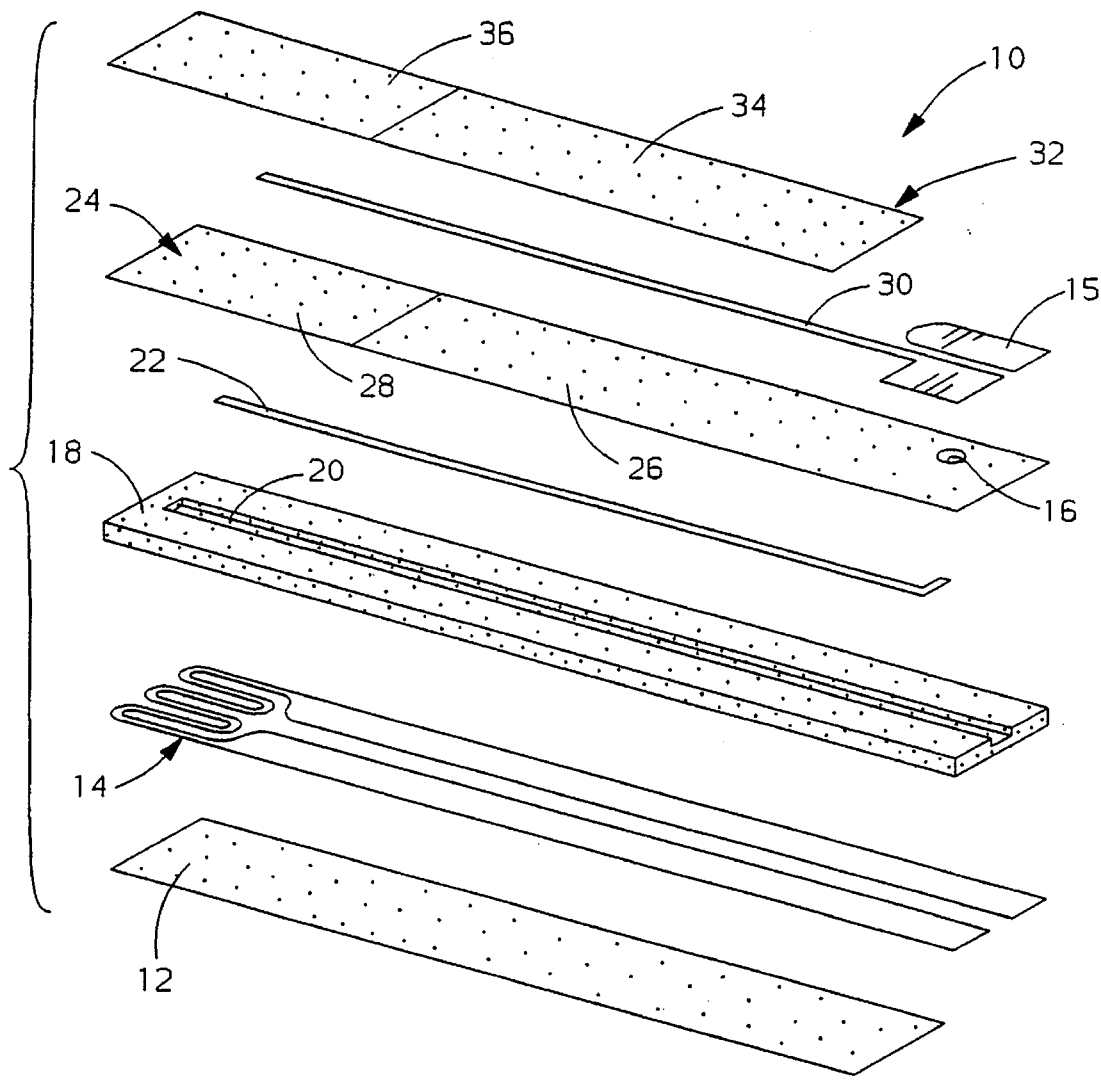
FIG. 2 is an exploded view of a flat plate sensing element useful in the present invention.

FIG. 2 illustrates an exhaust sensor 10 according to the present invention including, an overlapping relationship, the following elements: a heater dielectric protective tape 12; a printed heater 14; an alumina substrate 18 including an air reference channel 20 formed therein; an inner electrode 22 printed on one side of a co-cast composite tape 24 including a dielectric portion 26 and an electrolyte body portion 28; an outer electrode 30 and sensor pads printed on the other side of the co-cast composite tape 24; and a protective outer tape 32 including a dense alumina portion 34 and a porous alumina portion 36 overlying the electrolyte body portion 28 of the composite tape 24. The tape 24 has a hole 16 formed therein to provide contact between pad 15 and inner electrode 22. The co-cast composite tape 24 includes a first portion 26 which is a dielectric material such as alumina and the second portion 28 is a porous electrolyte material such as zirconia near one end of the sensing element 10. The co-cast composite tape 24 may be made from a variety of methods such as slurry casting, roll compaction or calendaring. Such processes are disclosed in U.S. patent application Ser. No. 08/196863 filed Feb. 15, 1994, now U.S. Pat. No. 5,384,003 assigned to the assignee of the present invention, the disclosure of which is hereby incorporated by reference. The various layers of the sensing element are fired together to form a single flat plate sensing element.

Figure 3:
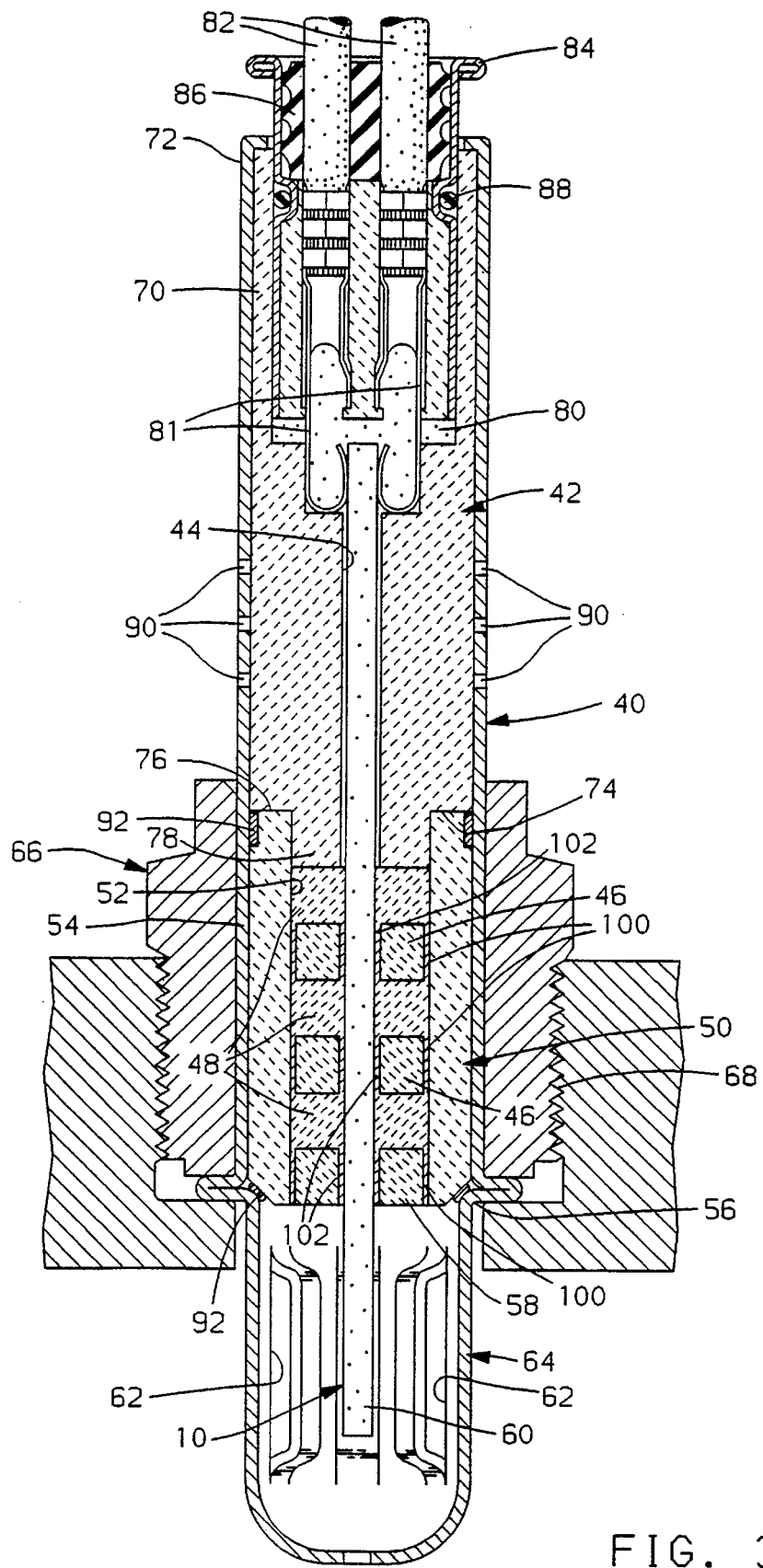
FIG. 3 illustrates an exhaust sensor according to the present invention.

The invention includes an exhaust sensor having a heated flat plate sensing element 10 as illustrated in FIG. 2 and described above or a conventional flat plate sensing element. As illustrated in FIG. 3, the flat plate sensing element 10 is carried in a metal tube or housing 40 and held in position by an upper ceramic locator 42 which is preferably made from steatite. Steatite is a mixture of talc, clay and alkaline-earth oxides and is available from Elan Co. The upper ceramic locator 42 has a hole 44 formed therein to receive the upper portion of the flat plate sensing element 10. The middle portion of the flat plate sensing element 10 has a middle sealing system surrounding it and includes a plurality of alternating spacers 46 (preferably steatite) and glass 48 layers. The glass layer may be formed from a glass frit preform, preferably borosilicate, which is sintered when the entire sensor package is heated in a furnace. The alternating layers of steatite 46 and glass 48 are surrounded by a ceramic tube 50 which is carried inside of the metal tube housing 40. The ceramic tube 50 has substantially straight inside 52 and outside 54 walls. The ceramic tube 50 is held in place by a crimp 56 formed in the metal tube housing 40 near the lower end of the ceramic tube 50. The lower end of the ceramic tube 50 is capped with a ceramic cap 58 which is preferably made of alumina.

The flat plate sensing element 10 includes one end 60 extending downward from the ceramic tube 50 and positioned to be exposed to exhaust gas travelling through holes 62 or louvers formed in an end cap 64 for the exhaust sensor. Preferably the exhaust sensor includes a slidably hex nut 66 having threaded portion 68 for engaging threads formed in a manifold boss in the exhaust system of the automotive combustion engine.

The upper end 70 of the ceramic locator 42 extends from the flat plate sensing element 10 to the top 72 of the metal tube housing 40. The ceramic locator 42 has a shoulder 74 formed therein for engaging the top 76 of the ceramic tube 50 and a nose 78 for engaging a first layer of glass 48 making up the middle sealing system. The upper steatite locator 42 may be used to plunge the various layers of the sealing system together before they are sintered in a furnace. The upper portion of the upper steatite locator 42 has a hole 80 formed therein to receive wires 82 for communicating with the flat plate sensing element. The ceramic locator 42 surround wire connectors 81 and the wires 82 prevent excess heat from damaging the same. The wires 82 are positioned using a tubular connector 84 having a Teflon seal or stopper 86 therein for holding the wires 82 in position. The tubular connector 84 may be frictionally held in place using an 0-ring 88. Reference air is provided to the sensing element 10 through the upper end of the sensor package. The metal tube housing 40 may have a plurality of vents 90 formed in the tube to reduce heat flow through the sensor package to lower the upper seal temperature.

A ceramic-to-metal braze 92 may be formed at various locations including the lower end of the ceramic tube 50 and the crimp 56 in the metal tube, or at the top outside wall of the ceramic tube, to hold the ceramic tube 50 and the flat plate sensing element 10 in a fixed position with respect to the metal tube housing 40.

The ceramic-to-metal braze 92 may be formed from an active metal braze material which includes silver, copper and titanium, which preferably are present in 59%, 40% and 1% by weight, respectively. A suitable active metal braze material is available from Lucas Milhaupt Inc., under the trade names BR559™.

The glass layer 48 preferably includes borosilicate and about 7 weight percent mullite for fracture toughness and equal distribution of the glass on hot pressing. Preferably the glass has a coefficient of thermal expansion of about 4.8 in/in° C. from room temperature to 250° C.; a glass transition temperature of about 468° C., and a softening point of about 696° C. The steatite layer 46 has a thermal of expansion of about 8.5 to 9.3 in/in° C. at 40°–900° C. The coefficient of thermal expansion of the alumina tube 50 and the heating element 10 having an alumina support substrate 18 are both about 8.3 in/in° C. at 40°–1000° C.

Each layer of glass 48 has a thickness ranging from about 0.1 inches to about 0.3 inches. The steatite layers 46 have a thickness ranging from about 0.1 inches to about 0.3 inches. The glass and steatite layers have a diameter that varies with the size of the package but preferably is about 0.2 inches to 0.3 inches. The walls of the ceramic tube 50 have a thickness ranging from about 0.02 inches to about 0.1 inches and a length ranging from about 0.5 inches to about 2 inches.

The upper ceramic locator 42, ceramic tube 50, plurality of alternating layers of glass 48 and steatite 46, and the electrolyte element 28 are heated together in a furnace at a temperature ranging from about 850° C. to about 950°. When the glass layer preform softens, the upper ceramic locator 42 is used to plunge the multiple layers together and form a good seal. Preferably, the ceramic tube 50, each steatite spacer 46 and sensing element 10 are assembled with sufficient tolerances, about 0.001 to about 0.010 inches, so that upon heating of the glass layer 48 and plunging, a thin layer of glass 100 flows down between one end of the spacer and the ceramic tube and a thin layer of glass 102 flows down between the inside edge of the spacer 46 and the sensing element 10. A load of about 1 to about 10 lbs. is applied to the steatite ceramic locator (plunger) 42 to compact the glass layer 48 and steatite layers 48 tightly around the sensing element 10. Alternatively, a weight of 0.25 to about 2.5 lbs. may be set on top of the plunger for glass compression through the heating process. The components are then sintered together in the furnace. The sintered product is cooled and brazed to the inside of the tubular-shaped metal housing 40. Other unique features and properties of the various components of the sensor package are as follows.

The flat plate sensing element 10 includes an alumina support substrate 18 and a zirconia porous electrolyte portion 28 for measuring the presence of various constituents within the exhaust gas stream. The ceramic tube 50 is preferably made from a ceramic oxide such as alumina, for example, 95 weight percent alumina, to have substantial strength and to substantially match the coefficient of expansion of the flat plate sensing element 10. The glass sealing layers 48 are utilized because they provide a good seal preventing exhaust gas from moving up through the sensor housing 40 and entering the air reference channel 20 of the sensing element 10. The various layers of steatite 46 are utilized because they have a coefficient of expansion similar to the alumina body 18 of the sensing element 10 and they provide good thermal resistance to heat flow through the sensor package which would prevent aid in reducing heat flow from the exhaust exposed end to the upper seal.

The use of a plurality of alternating glass 48 and steatite layers 46 within a ceramic tube 50 provides for a more compatible ceramic-to-ceramic seal formed with between the ceramic tube 50 and the plurality of layers 46, 48, and with respect to the plurality of layers 46, 48 and the sensing element 10. If there is a breakage in the seal, it is most likely to occur between the ceramic tube 50 and the metal tube housing 40. In such a situation, exhaust gas would flow between the metal tube housing 40 and the ceramic tube 50 up through the sensor housing 40 and out the vents 90 formed in the metal tube housing 40 or out the very top 72 of the metal tube housing 40 between the upper steatite locator 42 and the inside wall of the metal tube housing 40. The upper steatite locator 42 extends along the inside wall of the metal tube housing 40 from the ceramic tube 50 to the top of the metal tube housing 40. Thus, even if there is a leak, exhaust gas travelling along the inside wall of the metal tube housing 40 cannot reach the air reference channel 20.

The embodiments of the invention in which an exclusive property or privilege is claimed are defined as follows:

1. An exhaust gas sensor comprising:

a flat plate sensing element for measuring constituents in the exhaust gas from a combustion engine, said flat plate sensing element comprising an alumina support substrate having an air reference channel;

a metal tubular-shaped housing around the flat plate sensing element;

an upper ceramic locator for carrying an upper portion of the flat plate sensing element, a portion of said upper ceramic locator extending from the flat plate sensing element to the housing;

an inner sealing system comprising a plurality of alternating layers of glass and steatite surrounding the flat plate sensing element, said glass and steatite being furnace sintered as a package wherein at least two layers of glass and two layers of steatite are present;

a ceramic tube having substantially straight inside walls, said ceramic tube extending from the housing to the plurality of alternating layers of glass and steatite, said ceramic tube comprising alumina and constructed to have a coefficient of thermal expansion substantially matching a coefficient of thermal expansion of said flat plate sensing element and, said inner sealing system further comprising a layer of glass extending between said ceramic tube and each of said layers of steatite, and a layer of glass extending between the flat plate sensing element and each of said layers of steatite, and said upper ceramic locator extending along the inside walls of the metal tubular-shaped housing from the ceramic tube to the top of the metal tubular-shaped housing.

2. An exhaust sensor as set forth in claim 1 further comprising an alumina cap at a lower end of the ceramic tube and extending from the flat plate sensing element to the ceramic tube.

3. An exhaust sensor as set forth in claim 1 wherein said housing comprises a metal tube having a crimp formed therein for holding the ceramic tube in position within the housing.

4. An exhaust sensor as set forth in claim 3 further comprising an active metal braze formed between the lower end of the ceramic tube and the crimped portion of the metal tubular-shaped housing.

5. An exhaust sensor as set forth in claim 1 further comprising an active metal braze formed between the housing and an upper portion of an outer wall of the ceramic tube.

6. An exhaust sensor as set forth in claim 1 wherein said ceramic tube has substantially straight outside walls.

7. An exhaust sensor as set forth in claim 1 wherein said ceramic tube comprises 95 weight percent alumina.

* * * * *